United States Patent
Skala

(10) Patent No.: US 8,098,295 B2
(45) Date of Patent: Jan. 17, 2012

(54) IN-VIVO IMAGING SYSTEM DEVICE AND METHOD WITH IMAGE STREAM CONSTRUCTION USING A RAW IMAGES

(75) Inventor: Michael Skala, Zichron Yaaqov (IL)

(73) Assignee: Given Imaging Ltd., Yoqneam (IL)

( * ) Notice: Subject to any disclaimer, the term of this patent is extended or adjusted under 35 U.S.C. 154(b) by 1319 days.

(21) Appl. No.: 11/367,357

(22) Filed: Mar. 6, 2006

(65) Prior Publication Data

US 2007/0206092 A1 Sep. 6, 2007

(51) Int. Cl.
H04N 5/235 (2006.01)

(52) U.S. Cl. .......... 348/230.1; 348/77; 348/231.2; 600/109; 600/112

(58) Field of Classification Search ........... 348/77, 348/231.2, 231.3, 231.1, 230.1; 600/109, 600/112, 407, 425
See application file for complete search history.

(56) References Cited

U.S. PATENT DOCUMENTS

| | | | |
|---|---|---|---|
| 4,278,077 A | 7/1981 | Mizumoto | |
| 4,936,823 A | 6/1990 | Colvin et al. | |
| 5,604,531 A | 2/1997 | Iddan et al. | |
| 5,697,384 A | 12/1997 | Miyawaki et al. | |
| 5,836,877 A * | 11/1998 | Zavislan | 600/407 |
| 5,993,378 A | 11/1999 | Lemelson | |
| 6,167,402 A * | 12/2000 | Yeager | 1/1 |
| 6,240,312 B1 | 5/2001 | Alfano et al. | |
| 6,871,009 B1 * | 3/2005 | Suzuki | 386/230 |
| 7,009,634 B2 | 3/2006 | Iddan et al. | |
| 7,424,133 B2 * | 9/2008 | Schultz et al. | 382/106 |
| 7,522,825 B2 * | 4/2009 | Kenet | 396/14 |
| 7,564,579 B2 * | 7/2009 | Tipirneni | 358/1.15 |
| 7,583,298 B2 * | 9/2009 | Takasumi | 348/231.2 |
| 7,609,301 B2 * | 10/2009 | Kaku | 348/231.2 |
| 7,623,690 B2 * | 11/2009 | Cahill et al. | 382/128 |
| 2002/0037711 A1 * | 3/2002 | Mizutani | 455/414 |
| 2002/0103417 A1 | 8/2002 | Gazdzinski | |
| 2003/0043263 A1 | 3/2003 | Glukhovsky et al. | |
| 2003/0122942 A1 * | 7/2003 | Parker et al. | 348/231.3 |
| 2003/0167000 A1 | 9/2003 | Mullick et al. | |
| 2003/0208107 A1 | 11/2003 | Refael | |
| 2003/0222993 A1 * | 12/2003 | Hatano | 348/231.1 |
| 2005/0025368 A1 * | 2/2005 | Glukhovsky | 382/236 |
| 2005/0075537 A1 | 4/2005 | Chen et al. | |
| 2005/0159643 A1 | 7/2005 | Zinaty et al. | |

(Continued)

FOREIGN PATENT DOCUMENTS

DE 344 0177 5/1986

(Continued)

OTHER PUBLICATIONS

U.S. Appl. No. 11/631,367, filed Jan. 25, 2008, Nisani et al (PCT/IL2005/000696).

(Continued)

Primary Examiner — Tuan Ho
Assistant Examiner — Kent Wang
(74) Attorney, Agent, or Firm — Pearl Cohen Zedek Latzer, LLP

(57) ABSTRACT

A system, device and method for constructing an in-vivo image stream from in-vivo raw data base files. The in-vivo imaging system may include, for example an in-vivo imaging device, a receiver/recorder and a computing device such as a workstation a portable device and/or a portable memory.

20 Claims, 4 Drawing Sheets

U.S. PATENT DOCUMENTS

| | | | |
|---|---|---|---|
| 2005/0206746 A1* | 9/2005 | Cazier et al. | 348/231.2 |
| 2006/0158533 A1* | 7/2006 | Brahmbhatt et al. | 348/231.2 |
| 2006/0197838 A1* | 9/2006 | Yamakita | 348/169 |
| 2006/0226232 A1* | 10/2006 | Helkio et al. | 235/472.01 |
| 2007/0002730 A1* | 1/2007 | Lu et al. | 370/216 |
| 2007/0230893 A1* | 10/2007 | Meron et al. | 386/4 |

FOREIGN PATENT DOCUMENTS

| | | |
|---|---|---|
| JP | 57045833 | 3/1982 |
| JP | 4109927 | 4/1992 |
| JP | 1992-144533 | 5/1992 |
| WO | WO 03/010967 | 2/2003 |

OTHER PUBLICATIONS

Sippel H, Eich HP, Ohmann C. www.ncbi.nlm.nih.gov—Data collection in multi-center clinical trials via internet ;52 Pt 1:93-7, 1998.
www.ncbi.nlm.nih.gov—Data collection in multi-center clinical trials via internet. www.ncbi.nlm.nih.gov/pubmed/10179594, 1997.

* cited by examiner

IN-VIVO IMAGING SYSTEM DEVICE AND METHOD WITH IMAGE STREAM CONSTRUCTION USING A RAW IMAGES

FIELD OF THE INVENTION

The present invention relates to in-vivo imaging. More specifically the invention relates to a system device and method for receiving, recording, processing and presenting information gathered by an in-vivo imaging device.

BACKGROUND OF THE INVENTION

In-vivo devices, such as, for example, capsules having image capturing capabilities, may transmit streams of images while progressing through body lumens. Such a stream of images may be recorded in a memory of a recording device and may be used by human operators as, for example, a source of information regarding the health condition of such body lumens.

SUMMARY OF THE INVENTION

There is provided, in accordance with some embodiments of the present invention an in-vivo imaging system which may include an in-vivo imaging device, such as, for example, a capsule having image capturing capabilities, and a receiver/recorder, to receive information, for example in-vivo raw data which may include a stream of images, from the in-vivo imaging device and to store the raw data in a memory for a later use.

In addition, the in-vivo imaging system may include a workstation and/or a portable device, capable of downloading the raw data from the receiver/recorder and capable of creating in-vivo raw data base (RDB) files.

According to some embodiments of the present invention, the RDB files may include all the data needed to construct an in-vivo stream of images.

According to some embodiments of the present invention, after the RDB files are created the receiver/recorder may be reused for downloading new in-vivo raw data, for example from another in-vivo imaging device.

According to some embodiments of the present invention the in-vivo raw data may be inserted, for example by compressing, to a single file or to several files. Thus, the in-vivo raw data may be easily and quickly downloaded to, for example a portable memory, such as a DiskonKey, or may be manipulated to a computer network such as a public communication network e.g. the Internet or a cellular phone network.

BRIEF DESCRIPTION OF THE DRAWINGS

Embodiments of the invention are illustrated by way of example and not limitation in the figures of the accompanying drawings, in which like reference numerals indicate corresponding, analogous or similar elements, and in which.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. It will be appreciated that a variety of programming languages may be used to implement the teachings of the invention as described herein.

Figure 1A:
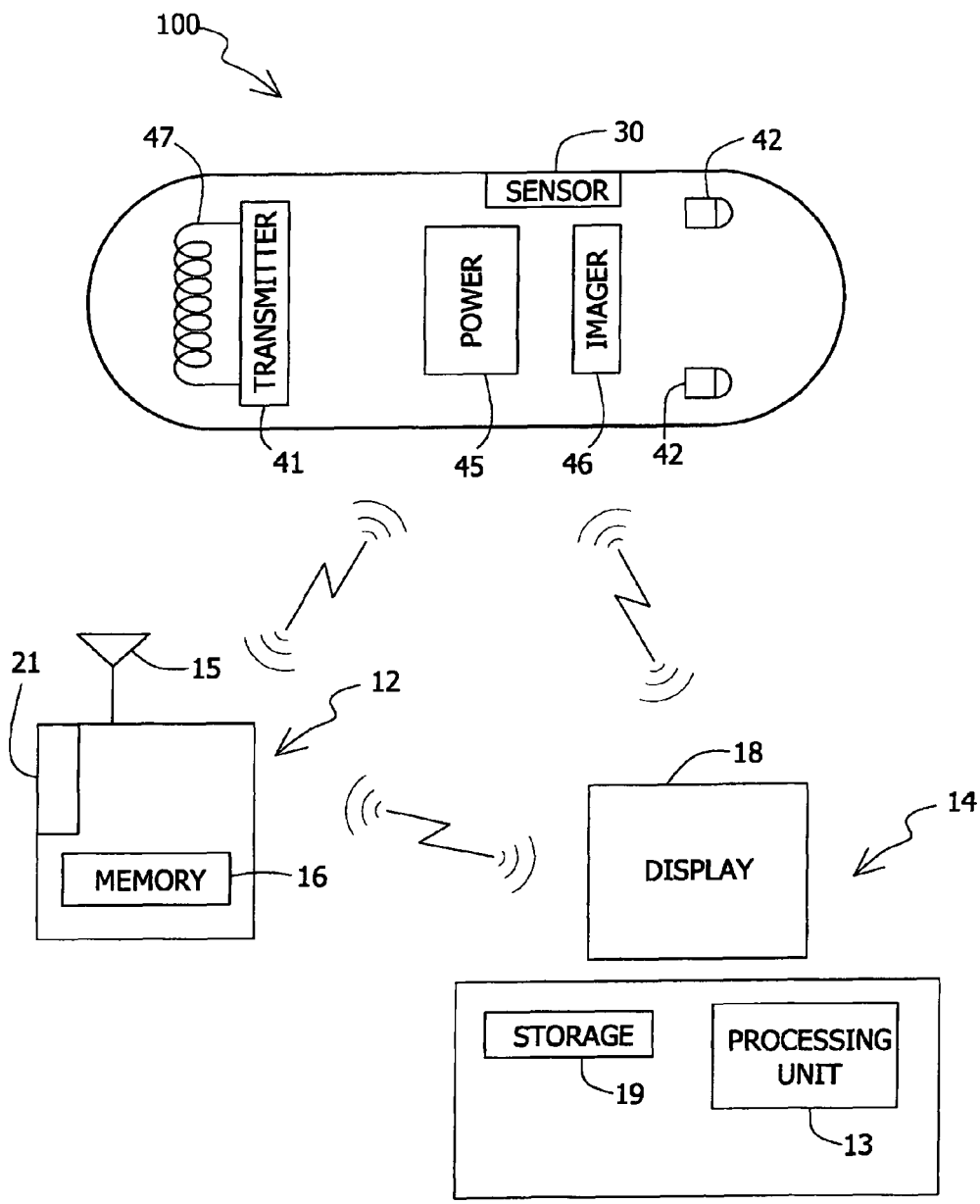
FIG. 1A is a schematic illustration of an in-vivo imaging system according to one embodiment of the present invention.

Reference is made to FIG. 1A, which shows a schematic diagram of an in-vivo imaging system 100 according to one embodiment of the present invention. The in-vivo imaging system 100 may include an in-vivo imaging device 40 having, for example an imager 46, for capturing images, an illumination source(s) 42 such as a white LEDs (Light Emitting Diode), OLEDs (Organic LED) or other illumination sources, for illuminating the body lumen, a power source 45 for powering device 40, and a transmitter/receiver 41 with antenna 47, for transmitting and/or receiving in-vivo raw data such as images, for example to or from an external device such as a receiver/recorder 12.

In some embodiments, imager 46 may include, for example, a CCD (Charge Coupled Device) camera or imager, a CMOS (Complementary Metal Oxide Semiconductor) camera or imager, a digital camera, a video camera, or other suitable imagers, cameras, or image acquisition components. According to some embodiments a 320×320 pixel imager may be used. Pixel size may be between 5 to 6 micron. According to some embodiments pixels may be each fitted with a micro lens.

Transmitter/receiver 41 may operate using radio waves; but in some embodiments, such as those where device 40 is or is included within an endoscope, transmitter/receiver 41 may transmit data via, for example, wire, optical fiber and/or other suitable methods. Other suitable methods or components for wired or wireless transmission may be used.

In one embodiment, all of the components may be sealed within the device body (the body or shell may include more than one piece); for example, the imager 46, the illumination sources 42, the power source 45, the transmitter/receiver 41 and the antenna 47, may all be sealed within the device body.

In some embodiments of the present invention, in-vivo device 40 may include one or more sensors 30 other than and/or in addition to imager 46, for example, temperature sensors, pH sensors, pressure sensors, blood sensors, etc. In some embodiments of the present invention, device 40 may be an autonomous device, a capsule, or a swallowable capsule. In other embodiments of the present invention, device 40 may not be autonomous, for example, device 40 may be an endoscope or other in-vivo imaging sensing device.

Devices according to embodiments of the present invention, including imaging, receiving, processing, storage and/or display units suitable for use with embodiments of the present invention, may be similar to embodiments described in U.S. Pat. No. 5,604,531 to Iddan et al., entitled IN-VIVO VIDEO CAMARA SYSTEM, and/or in U.S. patent application Ser. No. 09/800,470 entitled A DEVICE AND SYSTEM FOR IN-VIVO IMAGING, both of which are assigned to the common assignee of the present invention and which are hereby incorporated by reference. Of course, devices and systems as described herein may have other configurations and other sets of components.

The in-vivo imaging device 40 may, according to some embodiments of the present invention, transmit information such as in-vivo raw data e.g., images or other data to the receiver/recorder 12 possibly close to or worn on a subject. The receiver/recorder 12 may include an antenna or antenna array 15 and a data storage unit or memory 16. The receiver/recorder 12 may of course take other suitable configurations and may not include an antenna or antenna array. In some embodiments of the present invention, the data receiver/recorder 12 may, for example, include processing power and/or a LCD display for displaying image data.

According to some embodiments of the present invention, the receiver/recorder 12 may, for example, transfer the received data to a computing device 14, such as a workstation or personal computer, where the in-vivo raw data may be further analyzed, stored, and/or displayed to a user. Computing device 14 may typically be a personal computer or workstation, which may include standard components such as a processing unit 13, a memory, for example storage 19, a disk drive, a monitor 18, and input-output devices, although alternate configurations are possible. Monitor 18 may be a conventional video display, but may, in addition, be any other device capable of providing image, stream of images or other data. Instructions or software for carrying out a method according to an embodiment of the invention may be included as part of computing device 14, for example stored in storage 19. In some embodiments, the receiver/recorder 12 may include a link 21 such as for example a USB, blue-tooth, radio frequency or infra-red link, that may connect to antenna 15 or to a device attached to antennas 15.

According to some embodiments of the present invention the memory 16 may be fixed in or removable from receiver/recorder 12. A non-exhaustive list of examples of memory 16 may include any combination of the following: semiconductor devices such as registers, latches, electrically erasable programmable read only memory devices (EEPROM), not AND (NAND) flash memory devices, not OR (NOR) flash memory devices, non-volatile random access memory devices (NVRAM), synchronous dynamic random access memory (SDRAM) devices, RAMBUS dynamic random access memory (RDRAM) devices, double data rate (DDR) memory devices, static random access memory (SRAM), universal serial bus (USB) removable memory, compact flash (CF) memory cards, personal computer memory card international association (PCMCIA) memory cards, security identity module (SIM) cards, MEMORY STICK® cards, and the like; optical devices, such as compact disk read-write memory (CD ROM), and the like; and magnetic devices, such as a hard disk, a floppy disk, a magnetic tape, and the like. In some embodiments memory 16 may hold approximately 10 Gigabytes of memory.

Figure 1B:
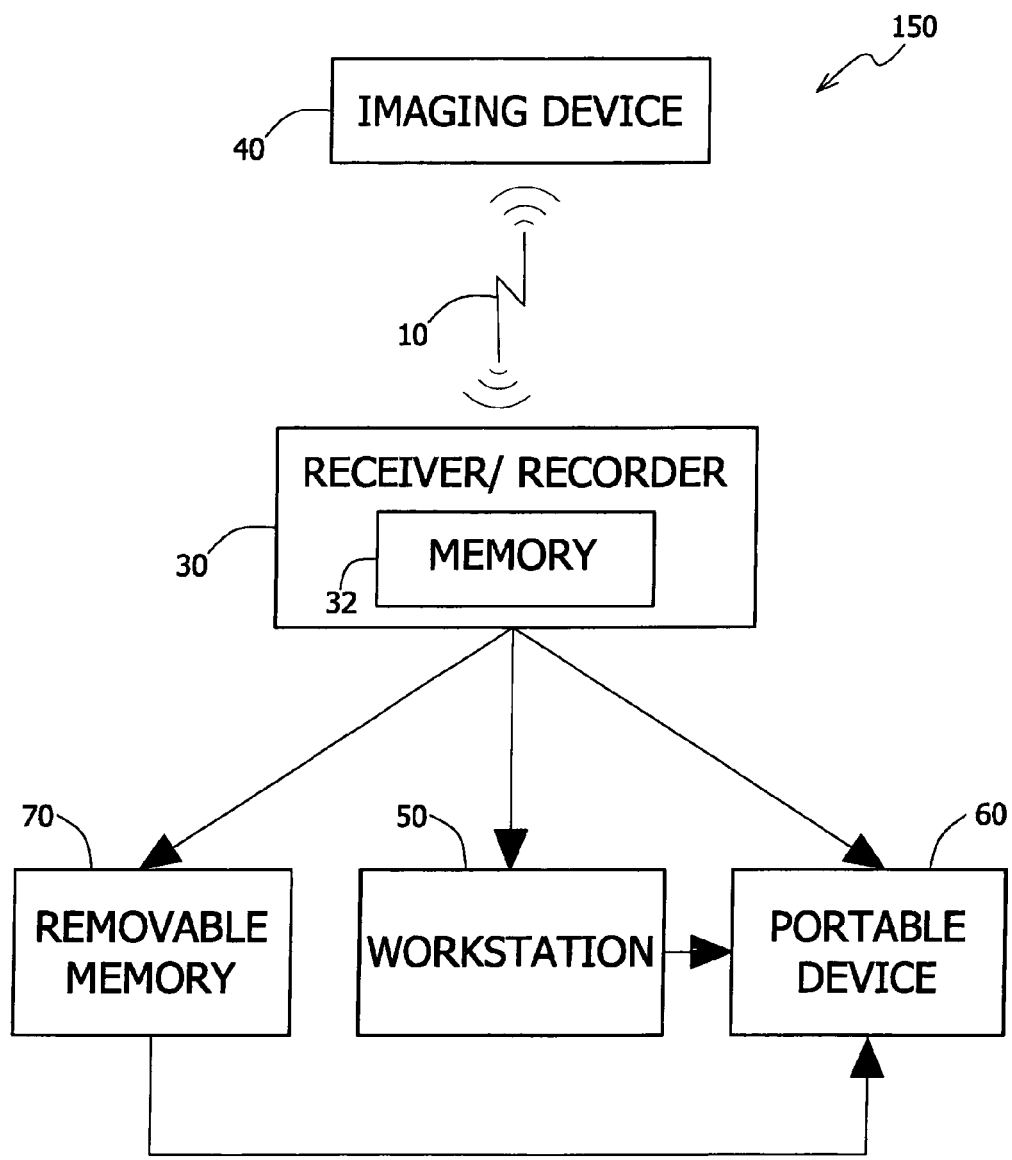
FIG. 1B is an exemplary simplified block-diagram illustration of an in-vivo imaging system, in accordance with another embodiment of the present invention.

FIG. 1B is a another illustration of an in-vivo imaging system 150, including for example an in-vivo imaging device 40, a receiver/recorder 30, a workstation 50 and a removable memory 70, in accordance with some embodiments of the present invention. In some embodiments, the portable device 60 may be for example a notebook or laptop computer, a personal digital assistant such as a SONY VAIO™ lightweight belt-portable computer.

As illustrated in the following description, device 40 may be able to gather information e.g. in-vivo raw data, while inside a patient's body. According to one embodiment of the present invention, the device 40 may be able to transmit at least that information to a receiver/recorder 30, for example, via a wireless or hard-wired medium 10 while inside the patient's body. According to one embodiment of the present invention, receiver/recorder 30 may include, for example a memory 32, and/or a buffer and may be able to record information received from the imaging device 40, for example on memory 32. According to one embodiment of the present invention, the receiver/recorder 30 may be able to transfer the received and/or recorded information to the portable device 60, and/or to the work station 50 via, for example, a wireless or hard-wired medium such as a USB cable.

According to some embodiments of the present invention, the information may be transmitted from the receiver/recorder 30 and/or may be transferred, for example through a removable memory 70, such as a DiskonKey or other small and portable memory device to the portable device 60 or the workstation 50.

Figure 2:
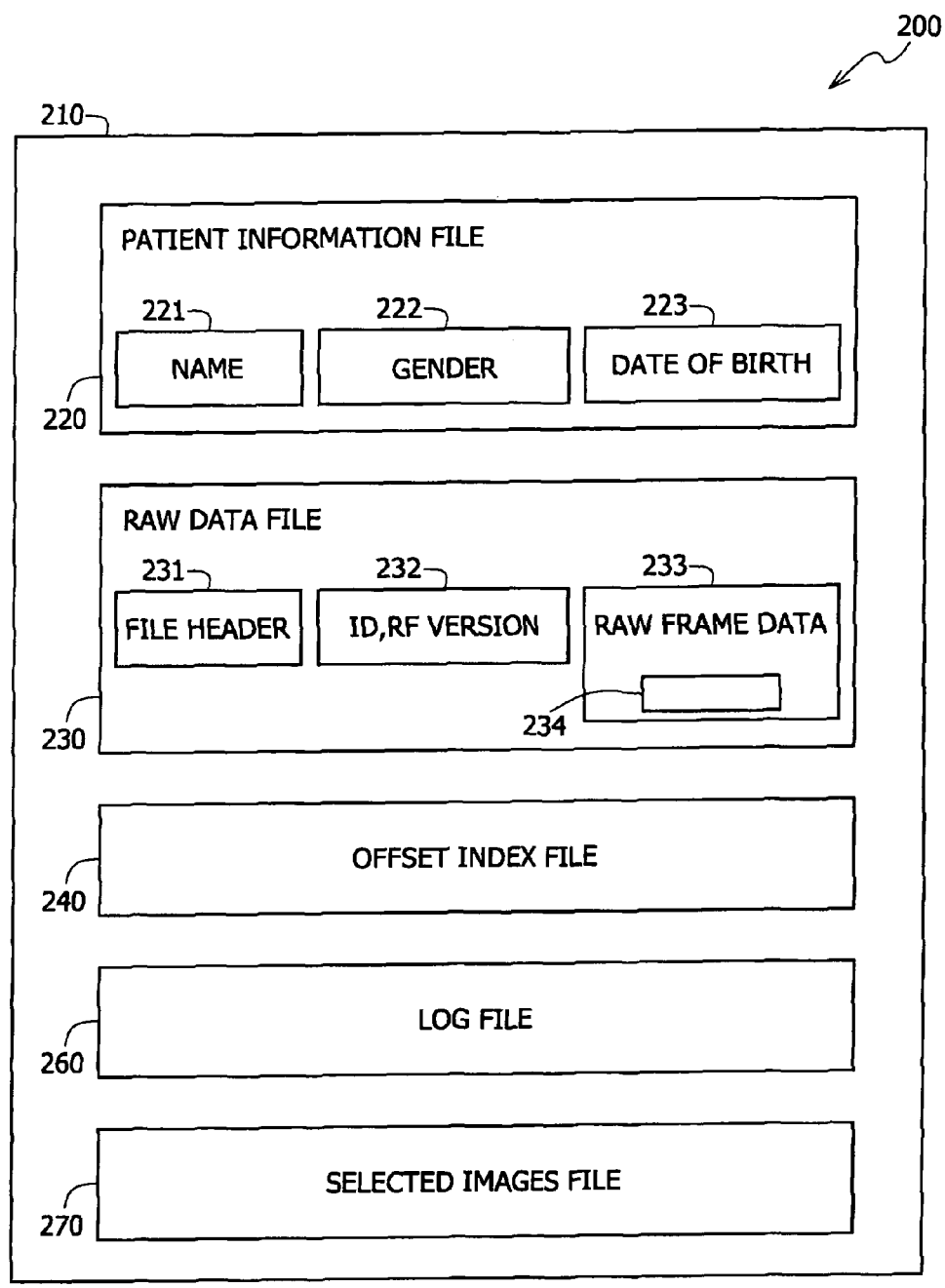
FIG. 2 is an exemplary block-diagram illustration of a data base format of an in-vivo imaging system, in accordance with some embodiments of the present invention.

FIG. 2 is an exemplary block-diagram illustration of an RDB format 200 of an in-vivo imaging system, such as system 100 of FIG. 1A, in accordance with some embodiments of the present invention. The RDB format 200 may be created in a computing device, such as workstation 14 and may include in-vivo RDB 210 which may be stored, for example, in a single folder at the storage unit 19 of the workstation 14. The in-vivo RDB 210 may be used to construct a stream of images captured for example by the in-vivo imaging device 40. According to one embodiment of the present invention processing unit 13 may operate software which, in conjunction with dedicated software may construct a stream of images from the in-vivo RDB 210.

According to some embodiments of the present invention, the in-vivo RDB 210 may include the following files: a patient information file 220, a raw data file 230, an offset index file 240 a recorder log file 260 and a selected images file 270.

The patient information file 220 may include, for example, patient data such as the name 221, the gender 222 and the birth date 223 of a patient.

According to some embodiments of the present invention, the raw data file 230 may be a binary file and may include three parts:

a) a file header 231.

b) hardware information 232 e.g. information regarding the hardware which was used for recording the raw data captured by the device 40, the hardware information 232 may include for example the serial number e.g. an ID number, of the receiver/recorder 12, the RF version of the imaging system etc.

c) raw frames data 233 e.g. the stream of raw images which were sent from the device 40 to the recorder/receiver 12. Each image of the stream of raw images may include a General Frame Data (GFM) 234 which may be inserted to each frame, for example by the receiver/recorder 12. The GFM may include for example a recorder frame header time e.g. the time the image was captured by the device 40, image size, image type, RSSI (Received Signal Strength Intensity), a synch header and raw scrambled data. In some embodiments the size of each frame in the stream of raw images may not be constant and may be changed, for example according to the image quality level.

According to some embodiments of the present invention, the raw frames data 233 may be inserted into a single file or into several files, for example by compressing the raw frames data 233. In some embodiments the number of files in the raw frames data 233 may be smaller then the number of raw images. In some embodiments each raw image in the raw frames data 233 may be accessed randomly.

The offset index file 240 may be used to find the offset of each frame in the raw frames data 233. The offset index file 240 may include for example two columns of numbers which may represent the ID number of each image and the size of each image. The offset of each image from the stream of raw images may be calculated according to the following formula:

Frame $i$ offset=HeaderSize+IdBlockSize+$\Sigma$abs(frame $j$ size)

($j$=0 ... $i$-1)

According to some embodiments of the present invention frames which do not meet a pre-set standard size constant parameter may be excluded during the raw image stream construction. For example if the size of frames X, Y and Z of image stream A is smaller then a pre-set standard size Sc the frames X, Y and Z will not be constructed during the construction of the raw image stream.

The recorder log file 260 may be a binary file, which may include a record of operation e.g. a log, which had occur during the downloading of information from the device 40 to the recorder/receiver 12. The log may be used for debugging problems in the in-vivo imaging system 100 such as recorder/receiver problems.

The selected images file 270 may include images such as "interesting" images which were selected from the raw frames data 233 according to predetermined criteria. For example, images pertaining to a known symptom, such as bleeding or ulcers. According to some embodiments of the present invention, the selected images file 270 may include a stream of dark images, such as dark images which may be sent from the receiver/recorder 12. The dark images may be used for canceling noise in the stream of images.

Figure 3:
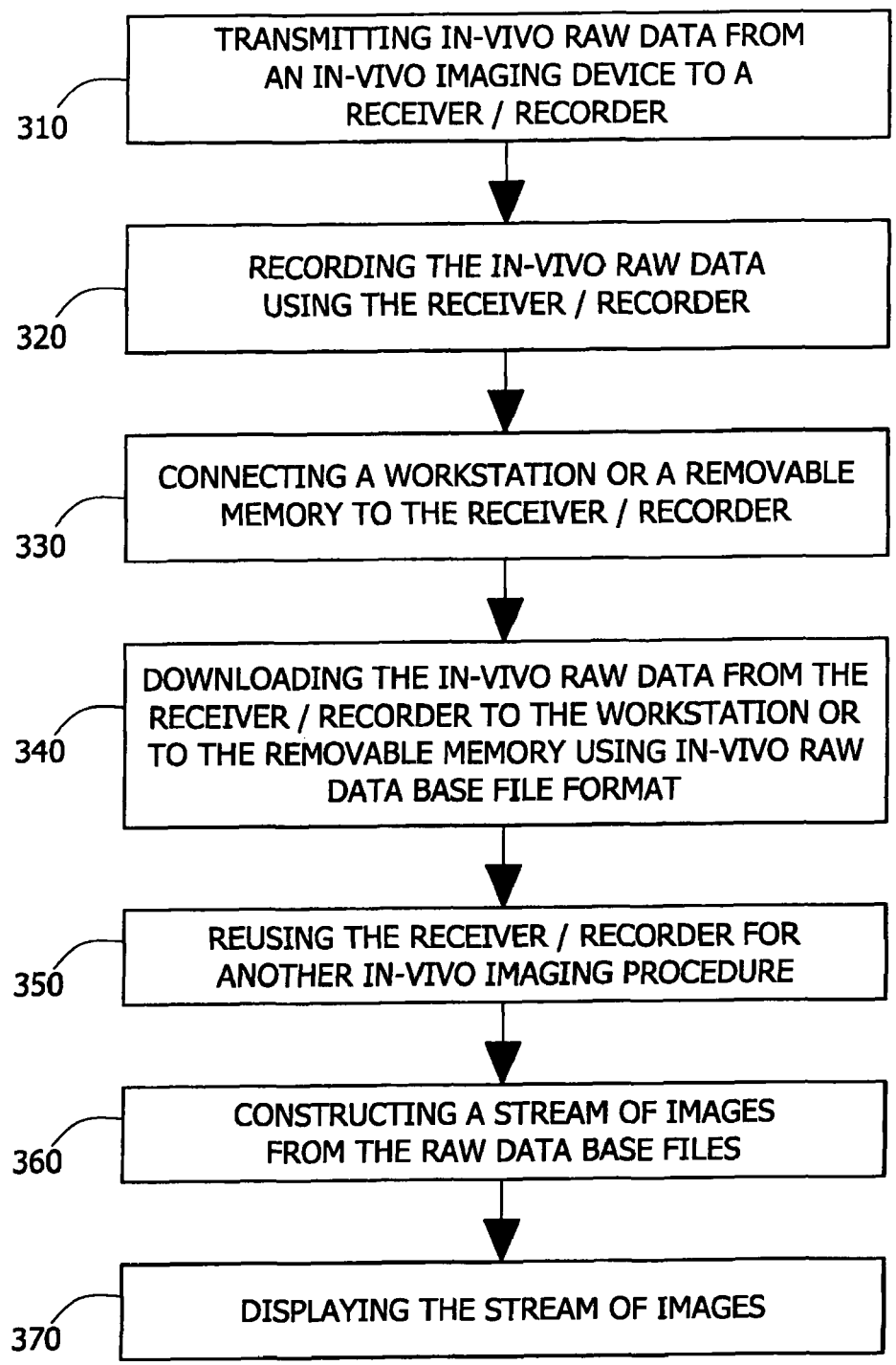
FIG. 3 is a schematic flow-chart of a method for receiving raw data from an in-vivo imaging device and constructing an image stream from the raw data, in accordance with some embodiments of the invention.

FIG. 3 is a schematic flow-chart illustration of a method for receiving information, such as in-vivo raw data captured by an in-vivo imaging device 40, and constructing an in-vivo image stream from the in-vivo raw data, according to some embodiments of the present invention. In step 310 an in-vivo raw data may be transmitted from the imaging device 40 to the receiver/recorder 30 for example by wireless communication e.g., radio communication. In step 320 the in-vivo raw data may be recorded, for example, using the receiver/recorder 30, on a storage unit or memory, such as memory 32. In step 330 a computing device such as the workstation 50 or the removable memory 70, may be connected to the receiver/recorder 30, for example via a USB controller or another suitable link. In step 340 the in-vivo raw data, as received from the imaging device 40, may be downloaded, for example from the receiver/recorder 30, to a computing device, such as the workstation 50 or to the removable memory 70, using for example the in-vivo RDB files format 200. According to some embodiments of the present invention, the in in-vivo raw data base files format 200 may include in-vivo raw data file 230 for storing raw images, in some embodiments the number of files in the in-vivo raw data file 230 is smaller than the number of raw images. According to some embodiments a command to start downloading in-vivo raw data may be activated automatically, for example by connecting the receiver/recorder 30 to the workstation 50 or to the removable memory 70 via, for example, the USB controller. In step 350 the receiver/recorder 30 may be reused for another in-vivo imaging procedure, for example for downloading a second in-vivo data from another patient using a second in-vivo imaging device. In step 360 a stream of images may be constructed from the in-vivo RDB files 210 which may be located, for example in the input path. In step 370 the stream of images may be displayed, for example by display 18.

According to some embodiments of the present invention the RDB files 210 may be transmitted to a computer network such as a public communication network e.g. the Internet or a cellular phone network.

It will be appreciated by persons skilled in the art that the present invention is not limited to what has been particularly shown and described hereinabove. Alternate embodiments are contemplated which fall within the scope of the invention

What is claimed is:

1. A method for constructing an in-vivo image stream from raw data files, the method comprising:
    transmitting in-vivo raw data from an imaging device to a receiver, the in-vivo raw data comprising raw frame data each raw frame data item comprising a raw image data and raw image size data wherein the size of each frame changes across frames;
    downloading the in-vivo raw data from said receiver to a computing device and storing the raw frame data in the computing device as one or more raw data files and downloading to and storing on the computing device hardware information; and
    constructing an in-vivo raw image stream from the raw data files, wherein frames which do not meet a pre-determined standard size parameter are excluded from image stream construction.

2. The method according to claim 1, comprising displaying the in-vivo raw image stream.

3. The method according to claim 1, comprising transmitting the in-vivo raw data from the receiver to a communication network.

4. The method according to claim 3, wherein the communication network is selected from the group consisting of the Internet network and a cellular phone network.

5. The method according to claim 1, wherein said downloading is activated automatically by connecting the receiver to the computing device and after downloading the receiver is reused for receiving additional in-vivo raw data.

6. The method according to claim 1, comprising compressing the in-vivo raw data files into a single file.

7. The method according to claim 1, comprising creating a log file.

8. The method according to claim 1, comprising creating an offset file.

9. The method of claim 8, comprising:
using an offset index file to find the offset of each frame in the one or more raw data files, wherein the offset index file comprises an identifier for each frame and the image size of each frame.

10. The method according to claim 1, comprising creating a patient file.

11. The method according to claim 1, comprising creating a selected images file.

12. The method of claim 11, wherein, the selected images file comprises a stream of dark images to cancel noise in the construction of the in-vivo image stream.

13. The method of claim 1, comprising:
inserting into each frame a value indicating the received signal strength intensity for the frame, wherein the size of each frame changes according to an image quality level.

14. An in-vivo imaging system comprising:
an in-vivo imaging device configured to transmit in-vivo raw data comprising raw frame data, each raw frame data item comprising raw image data and raw image size data, wherein the size of each frame changes across frames;
a receiver to receive the in-vivo raw data; and
a computing device configured to download the in-vivo raw data and to store raw frame data for the raw images and hardware information, and to construct an in-vivo raw image stream from the raw data files, wherein frames which do not meet a pre-determined standard size parameter are excluded from image stream construction.

15. The system according to claim 14, wherein the computing device comprises a patient file.

16. The system according to claim 14, wherein the computing device comprises an offset file.

17. The system according to claim 14, wherein the computing device comprises a log file.

18. The system according to claim 14, wherein the computing device comprises a selected images file.

19. The system according to claim 14, comprising a display.

20. The system according to claim 14, wherein the raw images comprise data selected from the list consisting of: a recorder frame header, an image capture time, image type, Received Signal Strength Intensity, a synch header and raw scrambled data.

* * * * *